United States Patent [19]
Uno et al.

[11] Patent Number: 5,429,805
[45] Date of Patent: Jul. 4, 1995

[54] NON-DISPERSIVE INFRARED GAS ANALYZER INCLUDING GAS-FILLED RADIATION SOURCE

[75] Inventors: Masahiro Uno, Hachioji; Hitoshi Okuyama, Tokyo; Mituru Ohishi, Hachioji; Kozo Akao; Mitsuo Taniyama, both of Hino, all of Japan

[73] Assignee: Fuji Electric Co., Ltd., Japan

[21] Appl. No.: 177,383

[22] Filed: Jan. 5, 1994

[30] Foreign Application Priority Data

Jan. 8, 1993 [JP] Japan ................................ 5-001440
Oct. 6, 1993 [JP] Japan ................................ 5-249612

[51] Int. Cl.6 ............................................ G01N 21/05
[52] U.S. Cl. .................................. 422/83; 250/339.12; 250/339.13; 250/339.06; 250/343; 356/436; 356/437; 422/82.09
[58] Field of Search ............ 250/339, 343, 345, 339.01, 250/339.02, 339.06, 339.07, 339.12, 339.13; 356/435–440; 422/82.09, 83

[56] References Cited

U.S. PATENT DOCUMENTS

| | | | |
|---|---|---|---|
| 3,851,176 | 11/1974 | Jeunehomme et al. | 250/343 |
| 3,860,344 | 1/1975 | Garfunkle | 250/345 X |
| 4,176,963 | 12/1979 | Fabinski et al. | 356/435 X |
| 4,271,124 | 6/1981 | Speeter | 422/82.09 |
| 4,794,255 | 12/1988 | Miyatake et al. | 250/343 |
| 5,155,545 | 10/1992 | Rinke | 356/437 X |

FOREIGN PATENT DOCUMENTS

59-87653  6/1984  Japan.

Primary Examiner—James C. Housel
Assistant Examiner—Arlen Soderquist
Attorney, Agent, or Firm—Parkhurst, Wendel & Rossi

[57] ABSTRACT

A non-dispersive infrared gas analyzer, with improved linearity in output concentration signal especially in measuring gas species of high concentration, includes a measuring cell into which a gas to be measured is fed, a non-selective infrared radiation sensor disposed on one side of the measuring cell, an optical band-pass filter disposed between the measuring cell and the infrared radiation sensor, and a nonselective infrared radiation source, disposed on the other side of the measuring cell and having an infrared radiation transmission window, wherein the radiation source further includes a gas filled therein at a predetermined partial pressure and the filled gas has at least a common partial molecular structure with the gas to be measured.

8 Claims, 3 Drawing Sheets

WAVELENGTH

NON-DISPERSIVE INFRARED GAS ANALYZER INCLUDING GAS-FILLED RADIATION SOURCE

BACKGROUND OF THE INVENTION

The present invention relates to a non-dispersive infrared gas analyzer that continuously measures on a real-time basis the concentration of each constituent in a multi-component gas sample.

DISCUSSION OF THE PRIOR ART

An infrared gas analyzer is used for continuously measuring on a real-time basis the concentration of each component in a gas sample that contains various gas components by selectively detecting the amounts of infrared radiation absorbed by the gas components. The infrared gas analyzer is widely used in various fields because of its excellent selectivity and a high measuring sensitivity.

Below, a conventional non-dispersive infrared gas analyzer and its operational principles are explained with reference to FIG. 2.

In FIG. 2, 1 denotes a measuring cell through which a specimen gas flows, 2 an infrared radiation source, 3 a rotating sector (a chopper) for chopping infrared rays emitted from the infrared radiation source 2 and for feeding the chopped infrared rays intermittently into the measuring cell 1, 4 a motor for driving the rotating sector 3, and 5 a detection block disposed on the side of the measuring cell 1 for detecting the infrared ray that emerges from the measuring cell 1. This detection block 5 has a band-pass filter 7B, for example, a multi-layered thin-film interference filter, for transmitting infrared rays in a wavelength range corresponding to one of the absorption wavelength bands of the gas component to be measured in the gas sample and an infrared radiation sensor 7A such as a pyroelectric or semiconductor sensor, which shows flat spectral sensitivity in the absorption band of the gas to be measured.

One of the filters 7B is paired to one of the sensors 7A and a plurality of the pairs (three units indicated by #1 through #3 in FIG. 2), each pair corresponding to one gas component in the gas sample, are set up to a detection unit 7, and the unit 7 is housed in sensor fitting block 6.

In such an infrared gas analyzer, an infrared ray emitted by the infrared radiation source 2 is optically modulated into an infrared ray 8, interrupted in the closing-motion cycles of the rotary sector 3, and enters the measuring cell 1, where the infrared ray of wavelength range intrinsic to the respective gas components in the gas sample is absorbed according to the concentrations of the gas components during transmitting through the measuring cell 1, and the infrared ray not absorbed by the gas component reaches the detection block 5. In the detection block 5, the infrared ray in the pass band wavelength of the band-pass filter 7B is converted to electric signal in the infrared ray sensor 7A in each detection unit 7, and is then outputted as a signal to represent the concentration of the gas component which shows infrared absorption in the pass band wavelength of the band-pass filter 7B.

When the gas sample contains a constituent gas molecule which has an electric dipolemoment responsive to an electric field, and when oscillation and rotation associated with the oscillation of the constituent gas molecule are excited by the oscillation field of the infrared ray, absorption wavelength range and absorption intensity are intrinsic to and determined by the molecular structure of the constituent gas.

The wavelength of an infrared ray $\lambda$ and the vibration frequency $\tau$ have an inverse relation $\lambda = D/\tau$, with light velocity C acting as an intermediary. Since, once the value of one of the terms is given, the other value can be derived, both factors will be used in the same way in the explanations given hereinafter.

FIG. 4 schematically illustrates infrared absorption spectra observed by a gas sample containing different concentrations (C1 through C4) of a specific component under a pressure of about one atmosphere.

In the infrared absorption spectra of the gas specimens, the absorption of infrared rays corresponding to variation in the rotation of the molecules excited by the oscillation of the molecules is observed as continuous spectra as shown in FIG. 4, adjoining the center wavelength $\lambda b$ corresponding to the vibration frequency of the molecular oscillation of the component gas molecules.

It is known that infrared absorption intensity is given by the Lambert-Beer's law expressed by the following formula (1).

$$I = I_0 \ldots \quad (1)$$

Where $I_0$ = Incident light intensity
$I$ = Transmitted light intensity
$c$ = Concentration of the gas component to be measured
$k$ = Absorption coefficient
$L$ = Transmission length of infrared rays in the sample gas Since the absorption coefficient (k) in the formula (1) represents an extent of infrared ray absorption, the infrared absorption spectrum shown in FIG. 4 is regarded as to represent the value of this absorption coefficient (k).

The absorption coefficient (k) takes a large value in the vicinity of the absorption center of the wavelength $\lambda b$, which corresponds to the vibration frequency of the molecular oscillation as shown in the figure, and takes a smaller value in a region away from the absorption center wavelength $\lambda b$. However, because infrared absorption depends on the variation in the rotation of molecules exited by the molecular vibration of the component gas molecules as described above, the infrared absorption is specific to and determined by the molecular structure of the component gas.

Since in the infrared gas analyzer, the light of a wavelength range corresponding to the infrared ray absorption wavelength band of the component molecules of the object to be measured, is guided into the infrared sensor 7A through the band-pass filter 7B, a signal (S) outputted by the sensor as a variation $\Delta I$ in the transmitted light intensity and the concentration (c) of the component gas to be measured are related to each other strictly by the following formula (2).

$$S = \int_{\lambda_1}^{\lambda_2} S_0 [1 - \exp\{-k(\lambda, c) cL\}] \, d\lambda \quad (2)$$

However, if the value of the absorption coefficient corresponding to the variation in the transmitted light intensity, derived by integrating the formula (2), is regarded as an average absorption coefficient for the molecules of the gas to be measured in the pass band wavelength range of the band-pass filter, explanation will be given hereinafter on the bases of the formula (1), because the formula (1) has been practically applied to the incident and transmitted light in the wavelength range over the integration range from $\lambda_1$ to $\lambda_2$.

Since the formula (1) has been applied to the incident light and transmitted light in the infrared gas analyzer as described above, the difference ($_\Delta$I) between the transmitted light intensity (I) and the incident light intensity ($I_O$) of the infrared ray is detected as the concentration signal (S) in the infrared radiation sensor 7A. In other words, the concentration signal (S) from the infrared gas analyzer is expressed by the following formula (3).

$$S \infty_\Delta I = I_O - I = I_O \{1 - \exp(-kcL)\} \tag{3}$$

On the other hand, by dividing the terms on both sides of the formula (1) by $I_O$, taking a logarithm of the two sides and employing developed logarithm formula, we obtain formula (4) on the basis of the assumption that the term exceeding the square of $_\Delta I/I_O$ may be omitted when the difference ($_\Delta$I) between the transmitted light intensity (I) and the incident light intensity ($I_O$) is sufficiently small.

$$\log I/I_O = \log(1 - _\Delta I/I_O) = _\Delta I/I_O = \log \exp\{-kcL\} = -kcL$$

that is, $$_\Delta I/I_O = S/I_O = kcL \tag{4}$$

This formula (4) shows that the sensitivity of an infrared gas analyzer is proportional to the cell length (L), if the variation $_\Delta$I in the incident and transmitted light intensities is not too large and a term exceeding the square of $_\Delta I/I_O$ can be omitted.

Incidentally, when an infrared gas analyzer is used to measure low-concentration gas components and high-concentration gas components simultaneously, a long sample cell is usually selected so that sufficient signal can be obtained when we want to measure low-concentration gas components.

When high-concentration gas components are measured using a long sample cell, the difference ($_\Delta$I) becomes so large that the approximation that leads to the formula (4) can no longer be applied, and the relation between the electric signal (S) detected by the infrared radiation sensor 7A and the concentration (c) of the gas components to be measured shows non-linearity, as expressed by the formula (3).

The formula (3) indicates that the electric signal (S) varies on a curve, which has an asymptotic line of a constant value ($I_O$), with the product kcL.

For this reason, if a highly concentrated gas component is measured with a cell relatively long with respect to the value of the absorption coefficient (k), a signal output for the concentration change saturates around a maximum gas concentration, whereas the amount of change in the value of S becomes smaller because of a decrease in the signal resolution. Even if a linearization circuit is used to electrically correct the non-linear relationship between the input and the output in such a case, the linearization circuit does not function in a region where the variation in signal output relative to the concentration change is small.

Therefore, an analyzer illustrated in FIG. 3 may sometimes be used, which includes a detection unit (7A', 7B') for measuring high-concentration gas components disposed close to the light source to shorten the cell length (L). By employing substantially short cell length, the value of kcL is reduced to avoid reduction in the variation of the signal output in the high-concentration region. However, this method is not always advantageous because it makes the construction complex.

It is possible to adopt another method, in which the pass band wavelength range of the band-pass filter is set within a narrow wavelength range with a small absorption coefficient (k) in the absorption band of the gas to be measured in order to reduce the value of kcL. One example of a pass band wavelength range of a band-pass filter, that is selected within a narrow region and has a small absorption coefficient (k), is illustrated as a region (a) in FIG. 4, which shows the absorption spectral characteristics of the infrared rays.

The selected region (a) is one which adjoins a region showing strong absorption and which has an absorption coefficient value (k) that varies greatly with the wavelength. Therefore, the relationship between the electric signal (S) detected by the infrared radiation sensor 7A and the concentration (c) of the gas component to be measured will vary greatly by the slight difference in center wavelength and band widths of the pass band wavelength range of the band-pass filter.

On the other hand, in a multi-layered thin-film interference band-pass filter, in which the pass band wavelength range is determined by the thickness of the thin film, it is extremely difficult to manufacture a filter by controlling the thickness of the film very accurately with an acceptable repeatability so that the aforementioned variation will be neglected.

For this reason, it is difficult to manufacture repeatedly an infrared gas analyzer with less variation in its characteristics by keeping the pass band wavelength of the band-pass filter within a narrow spectral region of a small absorption coefficient (k) in the absorption band of the gas to be measured.

SUMMARY OF THE INVENTION

Accordingly, an object of this invention is to provide an infrared gas analyzer that is suitable to measure the concentrations of high-concentration gas components using a long measuring cell that can stably measure low-concentration gas components, and to avoid saturation in an output signal while maintaining the linearity between the concentration and the output signal within an acceptable range.

It is also intended to provide a non-dispersive infrared gas analyzer that can simultaneously and continuously measure the low-concentration gas components and high-concentration gas components in a sample gas using an analyzer equipped with a single measuring cell.

To achieve the objects and in accordance with the purpose of the invention, as embodied and broadly described herein, the non-dispersive infrared gas analyzer of the present invention includes a measuring cell into which a gas to be measured is fed, a non-selective infrared radiation sensor disposed on one side of the measuring cell, an optical band-pass filter disposed between the measuring cell and the infrared radiation sensor, and a non-selective infrared radiation source, disposed on the other side of the measuring cell and having an infrared radiation transmission window, wherein the radiation source further includes a gas filled therein at a predetermined partial pressure and the filled gas has at least a common partial molecular structure with the gas to be measured.

In one variation of the present non-dispersive infrared gas analyzer, the filled gas is the same gas species with the gas to be measured.

In another variation of the present non-dispersive infrared gas analyzer, the filled gas is a gas species different from the gas to be measured, but the filled gas species has common partial molecular structure with the gas to be measured and shows infrared absorption substantially equivalent to the gas to be measured.

In still another variation of the present non-dispersive infrared gas analyzer, the optical band-pass filter has a pass band which matches to entire one of the absorption bands of the gas to be measured and the non-selective infrared radiation sensor shows a flat spectral sensitivity over the pass band wavelength of the optical band-pass filter.

Another non-dispersive infrared gas analyzer for measuring a plurality of gas species of the present invention includes a measuring cell into which a plurality of gas species to be measured is fed, a plurality of pairs of a non-selective infrared radiation sensor and an optical band-pass filter disposed on one side of the measuring cell, a non-selective infrared radiation source, disposed on the other side of the measuring cell and having an infrared radiation transmission window, wherein the radiation source further includes a gas filled therein at a predetermined partial pressure and the filled gas has at least a common partial molecular structure with one of the gas species to be measured.

In one variation of another non-dispersive infrared gas analyzer, the filled gas is the same gas species with one of the gas species to be measured.

In another variation of another non-dispersive infrared gas analyzer, the filled gas is different from the gas species to be measured but has a common partial molecular structure with one of the gas species to be measured and showing infrared absorption substantially equivalent to the one of the gas species to be measured.

In still another variation of another non-dispersive infrared gas analyzer, the optical band-pass filter has a pass band which matches to entire one of the absorption bands of one of the gas species to be measured and the non-selective infrared radiation sensor pairing to the one of the optical band-pass filter has a flat spectral sensitivity over the pass band wavelength of the pairing band-pass filter.

With the configuration described above, an infrared ray from which the ray in the absorption center wavelength band of the gas to be measured is removed by the gas filled in the radiation source, is emitted from the radiation source filled with the same kind of gas to be measured, fed into the measuring cell through the infrared transmission window, transmitted through the measuring cell, and then received by the infrared sensor.

During transmitting through the measuring cell, a part of the infrared ray is absorbed by the gas to be measured. The emitted infrared ray distributes over the wavelength range outside of the center absorption band of the gas to be measured, and the gas to be measured shows a small absorption coefficient (k) in the outside wavelength range.

On the other hand, since the wavelength of the infrared ray detected by the detection unit has its incident wavelength range limited by the optical band-pass filter and since the infrared ray around the absorption center wavelength band of the gas to be measured is removed in the infrared radiation source, the wavelength band of the infrared ray detected by the detection unit is confined within a relatively narrow wavelength range with a small absorption coefficient (k) of the gas to be measured.

Because only the wavelength region with a small absorption coefficient (k) of the gas to be measured remains as an effective detection wavelength band as described above, no saturation in absorption occurs even if high-concentration gas components are introduced into the measuring cell, and a relatively large signal change is outputted from the infrared sensor.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
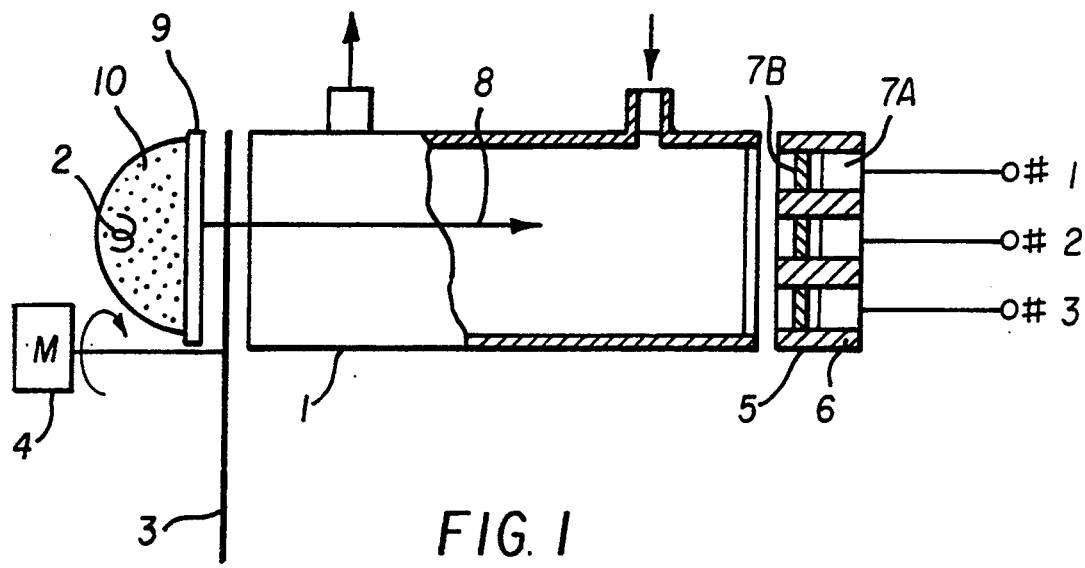
FIG. 1 is a cross sectional view showing the configuration of one embodiment of the present invention.

FIG. 1 shows a schematic cross sectional view of one embodiment of the present non-dispersive infrared gas analyzer and the present invention is explained with reference to this figure.

In FIG. 1, number 1 is a measuring cell through which a sample gas flows, and 2 is an infrared radiation source.

Figure 4:
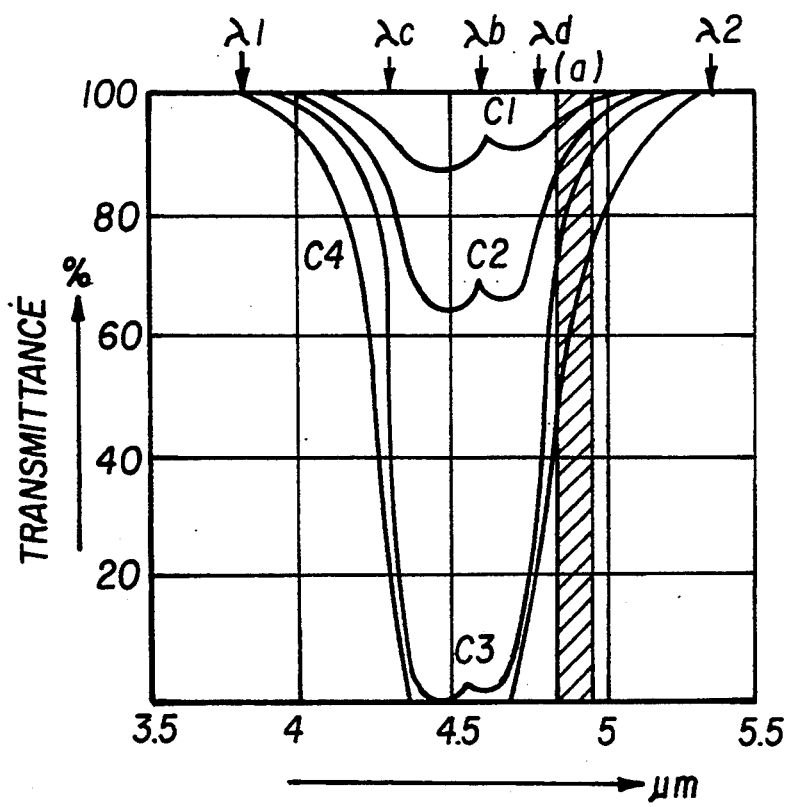
FIG. 4 is a descriptive chart to explain the infrared absorption spectra and pass band in an optical band-pass filter.

This infrared radiation source 2 is sealed with an infrared radiation transmission window 9, and is filled with a same kind of gas to be measured 10 at a predetermined partial pressure sufficiently high to absorb completely the infrared ray around the absorption center wavelength. By this configuration, an infrared ray, with its component of wavelength range around the absorption center wavelength of the filled gas removed and with its wavelength distribution as illustrated by C3 of the spectral figure in FIG. 4, is emitted from the infrared radiation source 2.

Incidentally, because the infrared ray is absorbed by gas according to changes in the rotation condition of molecules excited by the molecular oscillation of the constituent molecules of the gas components and because the absorption is determined by the structure of the component gas molecules, even different kinds of molecules will show the similar absorption in the wavelength range corresponding to common structural part of the molecules. Therefore, if the gas to be measured is active and unstable, it may be possible to replace the gas filled in the infrared radiation source with some other stable gas having the same structural portion as the gas to be measured. For instance, since nitrosyl chloride (NOCl), a synthetic textile starting material, is unstable and highly reactive, and is not desirable from the viewpoint of long-term safety to be filled in the infrared radiation source 2 in an infrared gas analyzer for measuring high-concentration nitrosyl chloride gas sample. Therefore, if chemically stable dinitrogen monoxide ($N_2O$), which shows an absorption wavelength band corresponding to the infrared absorption wavelength range of nitrosyl chloride because its molecular structure has the same nitrogen-oxygen bond (N-O) as nitrosyl chloride, is introduced into the infrared radiation source 2, the same function as that obtained when nitrosyl chloride is used is also obtained without causing corrosion in the infrared radiation source 2.

Next, 3 denotes a rotating sector (a chopper) that serves to interrupt (chop) the infrared ray emitted from the infrared radiation source 2, 4 a motor to drive the rotating sector 3, and 5 a detection block disposed on one side of the measuring cell 1 from which infrared ray emerges. This detection block 5 includes various infrared ray sensors 7A, each sensor corresponding to one of the gas components in the sample gas (three units indicated by #1 through #3 in the illustration) and an optical band-pass filter 7B such as a multi-layered thin film interference filter, for example, and the sensors and filters are paired to constitute the detection unit 7, which is arranged and housed in a sensor fitting block 6. A boundary wavelength of the pass band of the band-pass filter 7B for measuring high-concentration gas components is set to fall within the range of the wavelength range outside but in the vicinity of the absorption band of the gas to be measured, for example, within a range between $\lambda_1$ and $\lambda_2$ in FIG. 4, so that the boundary wavelength of the pass band will not fall within the region in which the absorption coefficient of the components to be measured greatly changes with the wavelength, even if some errors are caused in the boundary wavelength of the pass band during the manufacture of band-pass filter. On the other hand, the pass band of the band-pass filter 7B mounted in the detection unit 7 to measure low-concentration gas components is set in a range so that it falls within the absorption center band of the gas to be measured.

For the infrared radiation sensors 7A, sensors with a flat spectral sensitivity in the pass band of the band-pass filter 7B, such as a pyroelectric sensor or a semiconductor sensor, for example, are used.

With the configuration described above, a sufficient amount of the gas to be measured 10 is introduced at a predetermined partial pressure to absorb the infrared ray in the absorption center wavelength band of the infrared radiation source 2 in measuring high-concentration gas components to be measured. Since the infrared rays in the absorption center wavelength band are absorbed in the infrared radiation source 2, substantially no infrared ray in this wavelength band is fed into the measuring cell 1, and only the infrared ray in the wavelength band adjoining the absorption center wavelength range, in which absorption coefficient is small, is absorbed in the measuring cell 1.

Figure 5:
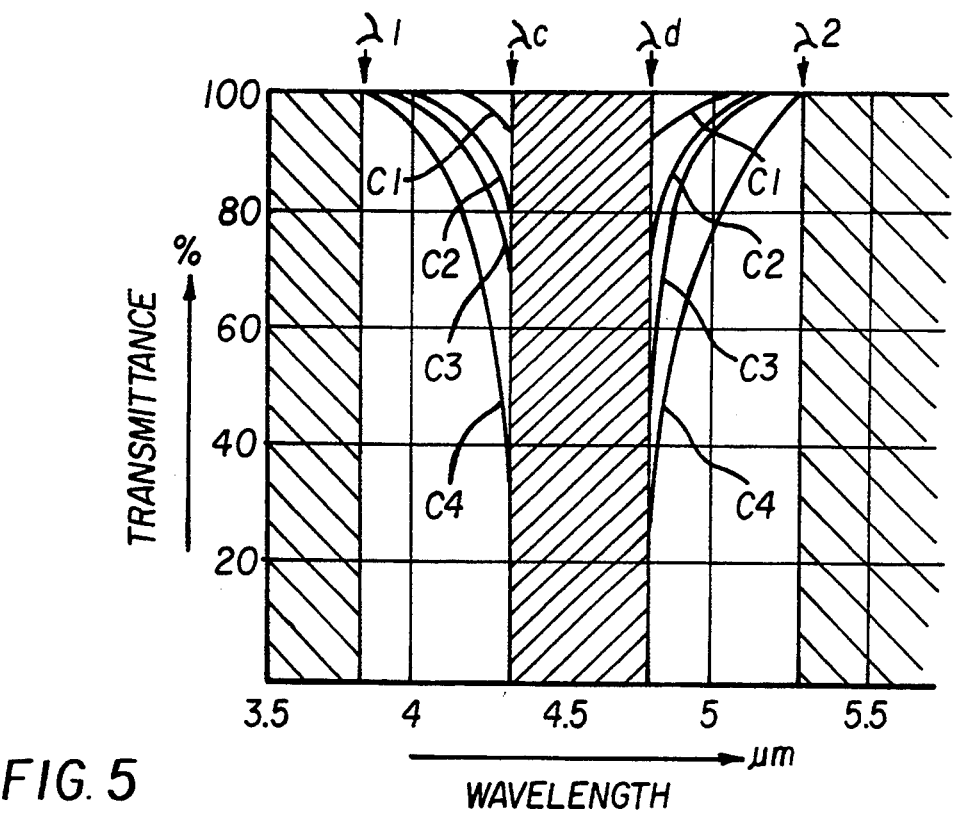
FIG. 5 is a descriptive chart to explain the wavelength range of the infrared rays detected in a detection unit for analyzing high-concentration gas components in the present infrared gas analyzer.

FIG. 5 graphically illustrates how absorption occurs in the measuring cell 1, and the wavelength distribution of the infrared ray inputted into the infrared radiation sensor 7A for analyzing high-concentration gas components.

In FIG. 5, $\lambda_1$, and $\lambda_2$ represent the boundary wavelengths in the pass band of the band-pass filter 7B. No infrared ray with wavelengths other than $\lambda_1$ and $\lambda_2$ is transmitted to the infrared radiation sensor 7A. Numbers $\lambda c$ and $\lambda d$ show the wavelength in the absorption center wavelength band of the high-concentration gas components. Since the gas components absorb most part of the infrared ray in the wavelength band, no infrared ray between these wavelengths enter the infrared radiation sensor 7A.

The infrared ray transmitted to the infrared radiation sensor 7A in the detection unit 7 for analyzing the high-concentration gas components falls within a wavelength range from $\lambda_1$ to $\lambda_c$ and $\lambda d$ to $\lambda_2$. In the wavelength bands from $\lambda_c$ to $\lambda d$ indicated by the hatching in FIG. 5, the infrared ray does not reach the infrared radiation sensor 7A.

Generally, none of the pass band of the optical band-pass filter or the absorption center wavelength band for the infrared ray have such sharp and well defined boundaries, as is schematically shown in FIG. 5. However, if we focus on the relationship in the relative intensity between the light entering the measuring cell 1 and the light transmitted out of the measuring cell 1 or the light detected by the infrared radiation sensor (7), the aforementioned schematic explanation would not lead to a distorted interpretation of the essence of the phenomenon.

As described above, because the infrared radiation sensor 7A used for analyzing high-concentration gas components detects infrared rays in a wavelength ranging from $\lambda_1$ to $\lambda_c$ with a small absorption coefficient (k) for the gas components to be measured (and from $\lambda d$ to $\lambda_2$), absorption by the high-concentration gas component will not saturate even when a long measuring cell is used, and the relationship between the output signal (S) and the concentration expressed by the formula 4, which gives a proportional relationship between (S) and (c), holds.

Figure 6:
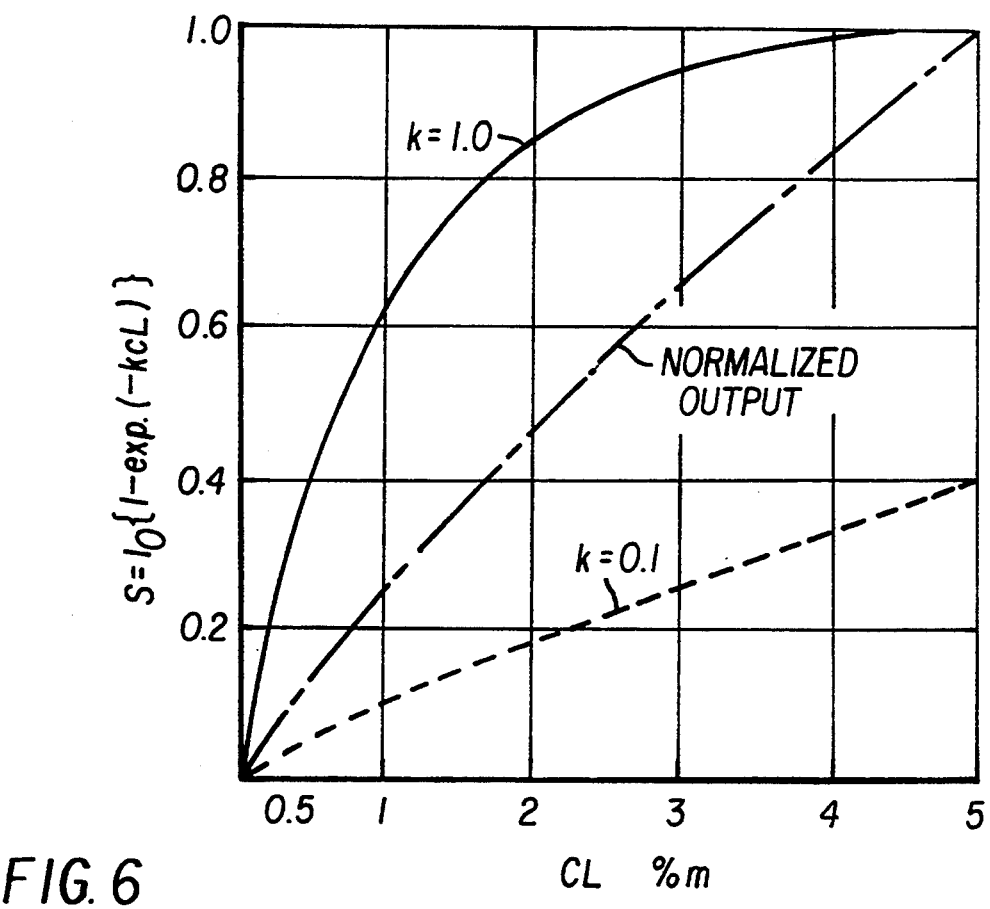
FIG. 6 is a graph to explain the effects of the absorption coefficient values on the relationship between the product of cell length and concentration, and output signals in an infrared gas analyzer.

FIG. 6 illustrates the relationship of the product (cL) of the concentration (c) of the gas to be measured and the cell length (L) of the measuring cell 1, and the output signal (S) from the detection unit 7.

Figure 2:
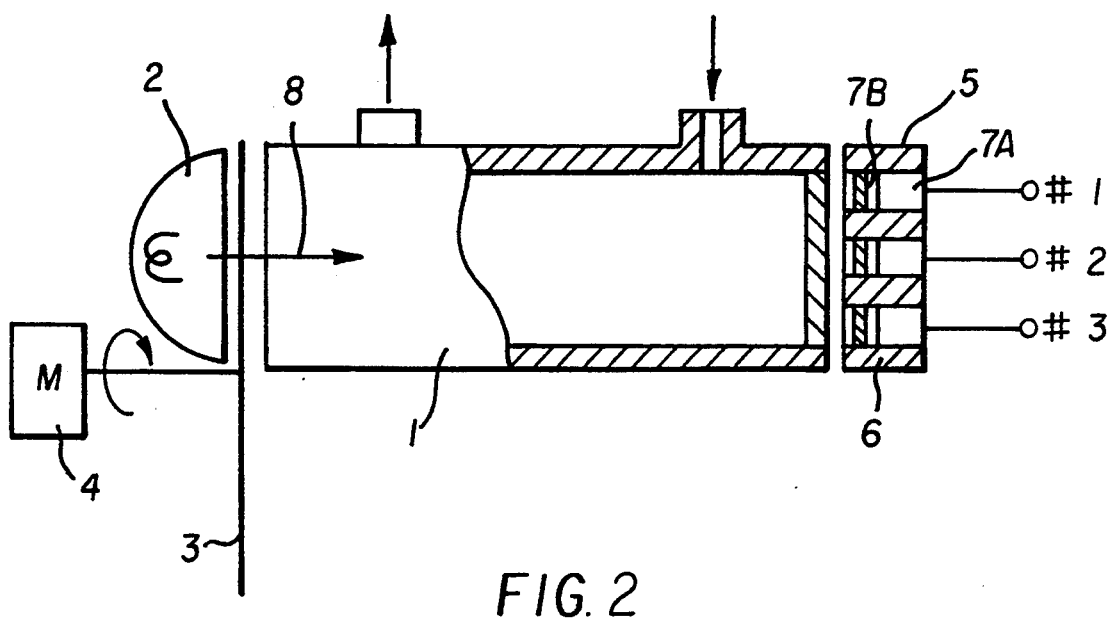
FIG. 2 is a cross sectional view showing the configuration of a conventional infrared gas analyzer.
Figure 3:
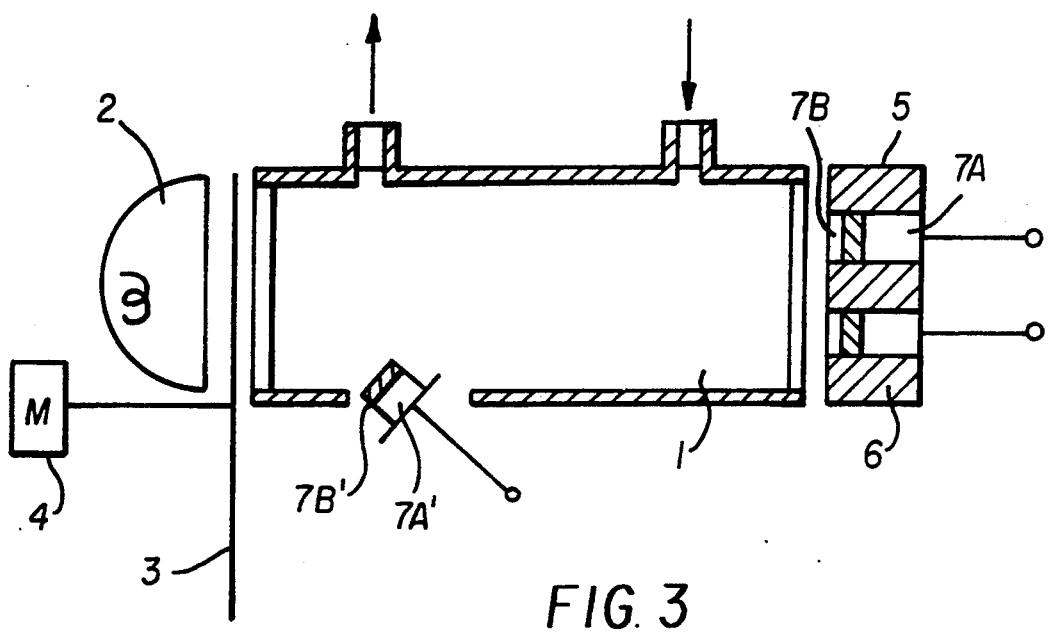
FIG. 3 is a cross sectional view showing the configuration of another conventional infrared gas analyzer.

In FIG. 6, the curve k=1.0 illustrates an analytical characteristic obtained by analyzing the high-concentration gas components by a conventional infrared gas analyzer shown in FIG. 2, that can analyze low- and high-concentration components simultaneously. In this conventional analyzer, the pass band of the optical band-pass filter of the detection unit 7 used to analyze high-concentration gas components is set to the absorption center wavelength band where infrared ray absorption is caused by the high-concentration gas components. As this curve shows, when the product of concentration and cell length exceeds 2%m and the value (k) is large, the output signal becomes saturated and change of the output signal with the cL becomes smaller with increasing cL.

In FIG. 6, the curve k=0.1 shows the relationship between the cell length-concentration product (cL) and the signal (S) output from the detection unit 7 when the value of the absorption coefficient for the gas components to be measured is selected at 1/10th of the absorption coefficient of the absorption center wavelength band, by restricting the detection wavelength band in the detection unit 7 for high-concentration gas components by the set up described above. In this case, the value of the output signal at a maximum concentration-cell length product of 5%m decrease to 40% of the value when the absorption coefficient is unity. FIG. 6 also shows a characteristic as the normalized output when this output at cL is 5% is amplified so that the value of the output signal at a maximum concentration-cell length product becomes equivalent to that in the case of $k=1.0$.

In the infrared radiation sensor, in which the detectable wavelength band in the detection unit 7 used to analyze high-concentration gas components is restricted by the set up described herein, the absolute value of the output signal (S) from the detection unit 7 may somewhat decrease, the proportional relationship is largely improved from the $k=1.0$ curve to the normalized output.

Thus by providing means for removing infrared rays in the absorption center wavelength bands, that are undesirable for measuring high-concentration component by the gas which contains the same kind of gas species with the gas to be measured which shows strong absorption in the absorption center wavelength range, on the basis of the fact that absorption wavelength bands depend on the molecular structure of the gas, the cut off wavelength range to be removed can be determined with greater accuracy than can be obtained by using an optical band-pass thin-film interference filter the pass band of which is determined by the control of the thin film thickness.

In addition, since the boundary wavelength of the pass band of the band-pass filter 7B disposed in the detection unit 7 used for measuring high-concentration gas components is designed to fall outside the infrared absorption wavelength region of the gas components to be measured so that the boundary wavelength does not fall in the absorption region in which the absorption coefficient of the gas components to be measured changes greatly with wavelength, even if there have been some errors in the manufacturing of the filter, the absorption in the wavelength range adjoining the absorption center wavelength band in the measuring cell occurs within the pass band of the optical band-pass filter. Therefore, the signal output from the infrared radiation sensor 7A for measuring high-concentration gas components becomes almost equivalent and represents the same amount of concentration change even if some manufacturing errors are committed in tuning the pass band of the band pass filter. Consequently, the relationship between the electric signal (S) from the infrared radiation sensor 7A and concentration (c) of the gas components to be measured will not vary by a slight difference in the center wavelength and the band width of the pass band of the optical band-pass filter 7B contrary to the disadvantage experienced in the conventional infrared gas analyzers, in which the pass band wavelength of the band-pass filter 7B is set within a narrow range with a small absorption coefficient (k) of the gas to be measured.

In an infrared gas analyzer for analyzing a plurality of gas components and for measuring low-concentration gas components and high-concentration gas components in a sample gas simultaneously and continuously, the boundary wavelength in the pass band of the band-pass filter 7B disposed in the detection unit 7 for measuring low-concentration gas components is set within a range superimposed on the absorption center of the gas components to be measured, and the sample cell is made as long as possible for realizing the stable measurement of low-concentration gas components.

For the measurement of the components of high concentration, a substitute gas that has an absorption wavelength band superimposed on the absorption wavelength band or the same gas with the gas species to be measured 10 is filled in the airtight infrared radiation source 2 at a partial pressure that is sufficiently high for completely absorbing the infrared rays in the absorption center wavelength of the gas species to be measured. And the boundary wavelength in the pass band of the optical band-pass filter 7B disposed in the detection unit 7 is set to a wavelength just outside the absorption band of the gas components to be measured, and the length of the measuring cell commonly used is set so that low-concentration gas components can also be measured.

If a non-dispersive infrared gas analyzer used to analyze various low- and high-concentration gas components is set up as described above, the infrared ray, in the absorption center wavelength band of a gas to be measured with a large absorption coefficient, is captured and measured with high sensitivity and stability for low-concentration gas components, while in high-concentration gas components, since the infrared rays, in wavelength bands with a small absorption coefficient and outside the absorption center wavelength band of the gas component to be measured, is captured and measured, analysis and measurements are conducted maintaining the linearity up to the high-concentration regions without saturation in the output even if a long measuring cell which is usually suitable for measuring low-concentration gas components is commonly used.

When the infrared gas analyzer for analyzing low-concentration gas components and high-concentration gas components simultaneously is set up according to the present invention, only the infrared ray in a wavelength band with a small absorption coefficient adjoining the absorption center wavelength band is absorbed in the measuring cell. Hence, absorption by high-concentration gas components is prevented from saturation even when a long measuring cell suitable for the measurement of low-concentration gas components is used. As a result, a measurement object, that shows non-linearity of 54% when measured by the conventional analyzer in which any kind of gas similar to the gas to be measured 10 is not filled in the infrared radiation source 2, is measured with improved non-linearity of 19% by the analyzer according to the present invention. In other words, an analyzer, which is equipped with a single measuring cell and is constructed simply and cheaply according to the present invention, is capable of measuring low- and high-concentration gas components accurately while maintaining acceptable linearity. Furthermore, since a gas components similar to the gas to be measured of high-concentration is filled in the infrared radiation source and since the infrared ray within wavelength band that is undesirable for measuring high-concentration components is removed in the radiation source, non-linearity tests and tuning on an individual analyzer using electrical circuits can be eliminated, because such an analyzer is manufactured by limiting the effective pass band to a relatively narrow range where sufficient change in the detection signal relative to the concentration change can be obtained and the characteristics between the concentration and output is stabilized even when an optical band-pass filter, with such a wide pass band that a sensitive wave length band in the detection unit for measuring high-concentration gas components corresponds to nearly the entire region of one absorption band of the gas to be measured, is employed.

Furthermore, inert gas may be filled in the radiation source for extending the life of the infrared radiation source. According to the present invention a gas filled in the radiation source may be replaced by the gas to be measured when the gas to be measured is $CO_2$ gas, thereby making a separate optical filter unnecessary, which serves to make the infrared gas analyzer more economical.

Furthermore, the set up according to the present invention can be employed not only to a multi-component infrared gas analyzer. The set up according to the present invention is employed also in an infrared gas analyzer for measuring high-concentration gas components with an absorption coefficient large enough to require to shorten the length of the measuring cell to an extent that would make it difficult to provide the measuring cell with a gas inlet or a gas outlet when an optical band-pass filter with the band corresponding to the absorption center wavelength band of the gas components to be measured is employed. In such a gas analyzer, the set up according to the present invention facilitates maintaining the cell length long enough to facilitate introduction and replacement of sample gas.

Other embodiments of the invention will be apparent to those skilled in the art from consideration of the specification and practice of the invention disclosed herein. It is intended that the specification and examples be considered as examples only, with a true scope and spirit of the invention being indicated by the following claims.

What is claimed is:

1. A non-dispersive infrared gas analyzer, comprising:
    a measuring cell into which a sample gas to be measured is fed;
    a non-selective infrared radiation sensor located adjacent to a first side of said measuring cell to receive an infrared ray that passes through the measuring cell along a defined path;
    an optical band-pass filter disposed between said measuring cell and said sensor in said defined path of the infrared ray; and
    a non-selective infrared radiation source located adjacent to a second side of said measuring cell opposite the first side, wherein said infrared radiation source is located within a sealed housing including an infrared radiation transmission window, wherein a gas is filled in said sealed housing at a predetermined partial pressure, and wherein said filled gas has at least a common partial molecular structure with said sample gas.

2. A non-dispersive infrared gas analyzer as claimed in claim 1, wherein said filled gas is comprised of the same gas species as said sample gas.

3. A non-dispersive infrared gas analyzer as claimed in claim 1, wherein said filled gas is comprised of a gas species different from said sample gas, said gas species of said filled gas having a common partial molecular structure with said sample gas and having an infrared absorption substantially equivalent to said sample gas.

4. A non-dispersive infrared gas analyzer as claimed in claim 1, wherein said optical band-pass filter has a pass band which matches to an entire one of the absorption bands of said gas to be measured and said non-selective infrared radiation sensor has a flat spectral sensitivity over said pass band of said optical band-pass filter.

5. A non-dispersive infrared gas analyzer for measuring a plurality of gas species, comprising:
    a measuring cell into which a plurality of sample gas species to be measured is fed;
    a detector structure located adjacent to a first side of said measuring cell to receive an infrared ray that passes through the measuring cell along a defined path, said detector structure including a plurality of non-selective infrared radiation sensors paired with corresponding optical band-pass filters;
    a non-selective infrared radiation source located adjacent to a second side of said measuring cell opposite the first side, wherein said infrared radiation source is located in a sealed housing including an infrared radiation transmission window, wherein a gas is filled in said sealed housing at a predetermined partial pressure, and wherein said filled gas has at least a common partial molecular structure with one of said sample gas species.

6. A non-dispersive infrared gas analyzer as claimed in claim 5, wherein said filled gas is comprised of the same gas species as said one of said sample gas species.

7. A non-dispersive infrared gas analyzer as claimed in claim 5, wherein said filled gas is comprised of a gas species different from said sample gas species, said gas species of said filled gas having a common partial molecular structure with said one of said sample gas species and having an infrared absorption substantially equivalent to said one of said sample gas species.

8. A non-dispersive infrared gas analyzer as claimed in claim 5, wherein one of said optical band-pass filters has a pass band which matches an entire one of the absorption bands of one of said gas species to be measured and said non-selective infrared radiation sensor corresponding to said one of said optical band-pass filters has a flat spectral sensitivity over said pass band of said one of said band-pass filters.

* * * * *